2 Claims, No Drawings

United States Patent
Satomura

[11] 3,933,885
[45] Jan. 20, 1976

[54] CINNAMYLIDENEACETIC ACID ESTERS

[75] Inventor: Masato Satomura, Asaka, Japan

[73] Assignee: Fuji Photo Film Co., Ltd., Minami-ashigara, Japan

[22] Filed: Feb. 12, 1974

[21] Appl. No.: 441,782

[30] Foreign Application Priority Data
Feb. 13, 1973 Japan .................... 48-17716

[52] U.S. Cl. ....... 260/465 D; 96/115 R; 204/159.15; 260/86.1 E; 260/89.5 R; 260/455 R; 260/469; 260/471 R; 260/473 R; 260/476 R; 260/479 R; 260/486 R; 260/558 P; 260/558 R; 260/559 R; 260/875
[51] Int. Cl.² .............. C07C 69/76; C07C 121/70
[58] Field of Search ....... 260/465 D, 476 R, 471 R, 260/473 R

[56] References Cited
UNITED STATES PATENTS
3,751,399  8/1973  Lee, Jr. et al ................. 260/476 X
3,817,876  1/1974  Fukutani et al ................ 260/476 X

*Primary Examiner*—Lewis Gotts
*Assistant Examiner*—Dolph H. Torrence
*Attorney, Agent, or Firm*—Sughrue, Rothwell, Mion, Zinn & Macpeak

[57] ABSTRACT

A monomer unit represented by general formula (I)

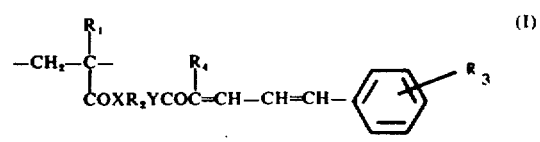

wherein $R_1$ is a hydrogen atom or a methyl group; $R_2$ is a divalent group containing 2 to 10 carbon atoms; $R_3$ is a hydrogen atom, a halogen atom (such as chlorine, bromine) a methoxy group, a nitro group or a methyl group; $R_4$ is a hydrogen atom, a cyano group or a carbamoyl group; X and Y each represents —O—, —S—, or —$NR_5$—; and $R_5$ represents a hydrogen atom, a methyl group or an ethyl group.

CINNAMYLIDENEACETIC ACID ESTERS

BACKGROUND OF THE INVENTION

1. Field of the Invention

The present invention relates to a copolymer of a polyacrylic acid derivative or a polymethacrylic acid derivative each having cinnamylideneacetic acid ester as a pendant group. More particularly, the invention relates to a functional group-containing polymer containing 1 to 90 mol percent of repeating units having a cinnamylideneacetic acid ester pendant group and also to a composition containing the functional group-containing polymer. The invention relates further to a method of preparing the functional group-containing polymer.

2. Description of the Prior Art

Various investigations have hitherto been made on systems which undergo changes in solubility, adhesiveness, or hardness at portions irradiated with light, thermal radiations, particle rays, electromagnetic waves, etc., and some of such systems are now being practically used.

With regard to functional group containing or reactive compounds employed in such conventional techniques, studies are known on $\alpha,\beta$-unsaturated carboxylic acid derivatives and $\alpha,\beta$-unsaturated carbonyl compounds as described in, e.g., J. Kosar; *Light Sensitive Systems;* Chapter IV, John Wiley & Sons, New York, 1965, and A. Schönberg; *Preparative Organic Photochemistry;* Chapter 8, Springer-Verlag, New York, 1968, studies on the photocyclobutane ring-forming addition reaction of cinnamic acid derivatives of these unsaturated carboxylic acids as described in, e.g., P. Silber; *Ber. Dtsch. Chem. Ges.*, 35, 4128 (1902), and studies on polymers containing cinnamic acid ester groups for applications to photosensitive systems as described in, e.g., A. Schönberg; *Preparative Organic Photochemistry*, Springer-Verlag, Chapter 8 as described above and also as described in the specifications of U.S. Pat. Nos. 2,835,656; 3,357,831; 3,737,319; 3,418,295; 3,647,470; 3,409,593; 2,956,878; 3,173,787; 3,023,100; and 3,066,117.

The aforesaid polymers containing cinnamic acid esters as the functional groups are those prepared by the reaction of hydroxy group-containing polymers (e.g., polyvinyl alcohol) and cinnamic acid esters. However, since polyvinyl alcohol is only sparingly soluble in ordinary solvents, there are disadvantages in that a large amount of solvent such as pyridine is required, a very long period of time is required for completing the reaction, and colored polymers are obtained. To minimize or eliminate these aforesaid disadvantages encountered in the production of these polymers, preparation of the polymer esters in the presence of an inorganic base at low temperature utilizing a Schotten-Baumann method has been the approach used, but since the reaction system is heterogeneous, it is difficult to control the temperature of the reaction system using this method.

In addition to the above-described disadvantages in the production of the polymers, there is also the disadvantage that the specific sensitivity of cinnamic acid esters is much lower than that of cinnamylideneacetic acid. Therefore, attempts to obtain polymers having cinnamylideneacetic acid esters as pendant groups have been made.

For instance, a method (1) wherein a functional group-containing polymer is obtained by reacting polyvinyl alcohol and cinnamylideneacetic acid chloride and a method (2) wherein a functional group-containing polymer is obtained by polymerizing a vinyl ether or a styrene derivative each having a cinnamylideneacetic acid ester group using an ionic polymerization initiator as a catalyst are known.

However, since method (1) is a reaction in a heterogeneous system at low temperature, the operations required for controlling the rate of reaction and reaction temperature are complicated.

For example, in U.S. Pat. No. 3,257,664, detailed experimental conditions concerning the reaction of a polymer (polyvinyl alcohol) with cinnamylidenacetyl chloride are described as follows:

a. in Example 4, a mixture of 22 g of polymer and 200 ml of pyridine was heated on a steam bath for 1 hour with stirring and an additional 200 ml of pyridine is added before the dropwise addition of melted cinnamylideneacetylchloride. The reaction is further conducted at 50°C for 4 hours. The yield is about 91 percent.

b. in Example 7, 380 ml of pyridine is used to swell (not to dissolve) 22 g of a polymer (polyvinyl alcohol) on a steam bath overnight. After the reaction of the polymer with an acid halide, the reaction mixture is heated at 50°C for 4 hours and diluted with 700 ml of acetone before precipitation into cold water. The resulting polymer is further purified by washing with water 4 times.

In these Examples, the polymer concentration is only 5.5 to 5.8 weight percent to the base (pyridine). Yet, as shown in the disclosure quite clearly, the polymer is only swollen by pyridine. That is, a heterogeneous, complicated reaction is contemplated from these reaction conditions.

To overcome these difficulties shown in U.S. Pat. No. 3,257,664, a modified process has been developed to obtain a cinnamylideneacetoxy functional group-containing polymer as described in U.S. Pat. No. 3,761,280 as follows.

In the Example, an isocyanate group containing cinnamylideneacetate is reacted with a polymer (polyvinyl alcohol). The isocyanate is used because it is more reactive with hydroxyl groups than an acid halide. Unfortunately, although the isocyanate must be synthesized using very complicated procedures such as using poisonous conditions as through phosgenation, a highly light sensitive functional polymer is obtained. However, the polymer concentration is only 5 weight% (that is 10 g of polymer is swollen in 200 ml of pyridine) and the reaction is conducted at 50°C for 3 hours.

The reaction conditions shown above are very severe, heterogeneous and complicated compared with those of the present invention (i.e., wherein homogeneous, mild reaction conditions are employed) as will be described hereinafter.

In addition, since method (2) utilizes an ionic polymerization reaction, the method is accompanied with the disadvantages that the polymerization reaction is greatly hindered due to the influence of humidity or moisture with the reaction sometimes ceasing completely, the operation conditions for conducting the reaction are complicated as a result of the low-temperature system, and further only gelled products are obtained using radical polymerization.

An object of this invention is to provide a novel functional group-containing polymer which can be easily prepared using a homogeneous reaction system without being accompanied by the aforesaid disadvantages.

Another object of this invention is to provide a method of preparing the functional group-containing polymer.

Still another object of this invention is to provide a reactive composition containing the functional group-containing polymer.

The inventors have already investigated acrylates or methacrylates each having a cinammic acid ester group and also the polymerization of such as described in U.S. Pat. No. 3,770,443. The present invention is an extension and improvement of our previous invention.

SUMMARY OF THE INVENTION

The present invention provides a functional group containing polymer containing 0.1 to 90 mol percent, in particular 1 to 60 mol percent, of the monomer unit represented by the general formula (I)

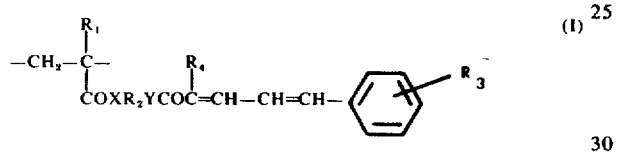

wherein $R_1$ represents a hydrogen atom or a methyl group; $R_2$ represents a divalent group having in total 2 to 10 carbon atoms; $R_3$ is a hydrogen atom, a halogen atom (such as a chlorine atom, a bromine atom), a methoxy group, a nitro group or a methyl group; $R_4$ is a hydrogen atom, a cyano group or a carbamoyl group; X and Y each represents —O—, —S—, or —$NR_5$—; and $R_5$ represents a hydrogen atom, a methyl group or an ethyl group.

DETAILED DESCRIPTION OF THE INVENTION

The functional group containing polymer of this invention can be used in various applications, such as for paints, coatings, adhesives, etc., for which compounds or compositions curable by electromagnetic waves or particle rays have conventionally been utilized but the functional group-containing polymer of this invention is particularly useful for forming relief images, printing plates, and photographic duplications.

Suitable examples of divalent groups having in total 2 to 10 carbon atoms are divalent groups such as alkylene, alkenylene, arylene, halogenated alkylene, cycloalkylene, oxa-alkylene, thiaalkylene, etc., groups.

Of the compounds represented by the general formula (I) the most preferred ones are those represented in which X and Y each is —O—. The following detailed description, for convenience, is with reference to the compound represented by the general formula (I) in which X and Y are —O—, but it will be appreciated that the description is applicable to all of the compounds of the general formula (I).

The functional group containing polymer containing the above-described monomer unit can be prepared using either of the following two methods (A) or (B).

A. Method utilizing a vinyl polymerization reaction:

The functional group containing polymer is prepared by polymerizing a monomer represented by the general formula (II)

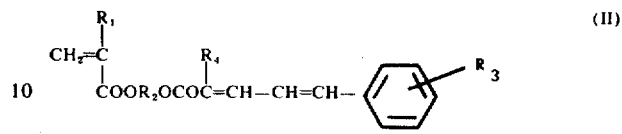

wherein $R_1$ has the same significance as in general formula (I);

$R_2$ represents, from a practical standpoint, —$CH_2CH_2$—, —$CH_2CH_2CH_2$—, —$CH_2CH_2CH_2CH_2$—, $$-CH_2-CH-,\ -CH_2-CH-,\ -CH_2-CH-,$$
$$\phantom{-CH_2-}CH_3\phantom{xx}CH_2Cl\phantom{xx}C_2H_5$$

—$CH_2CH_2OCH_2CH_2$—,

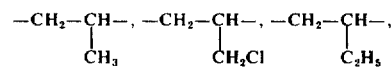

—$CH_2CH_2OCH_2CH_2OCH_2CH$—,
—$CH_2CH_2CH_2CH_2CH_2CH_2$—,

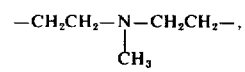

—$CH_2CH_2SCH_2CH_2$—, —$C_6H_{10}$—, —$C_6H_4$—, —$CH_2C_6H_4CH_2$—, or —$CH_2C_6H_{10}CH_2$—;

$R_3$ is a hydrogen atom, a halogen atom (such as chlorine or bromine), a methoxy group, a nitro group or a methyl group; and $R_4$ is a hydrogen atom, a cyano group or a carbamoyl group.

Examples of the particularly useful monomers of formula (II) for the production of the functional group containing polymer of this invention are as follows:

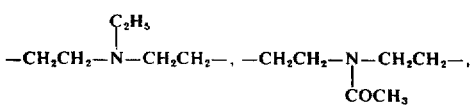

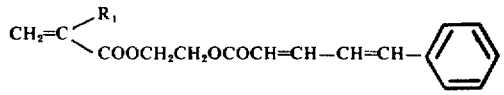

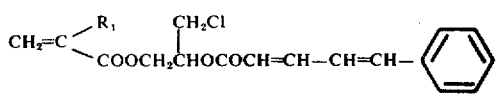

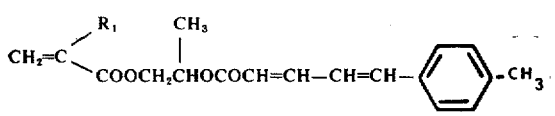

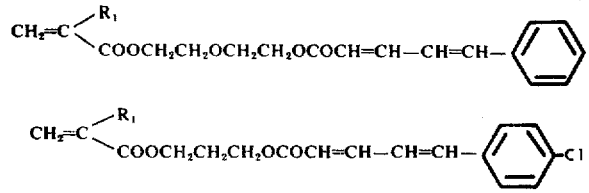

Each of the above-described monomers can be prepared (1) using a method in which a hydroxyl group-containing acrylate or methacrylate is employed as the starting material or alternatively (2) using a method in which a hydroxyl group-containing cinnamylidene acetate is used as the starting material (3) or other methods in which a halogen atom-containing acrylate or methacrylate is used as a starting material. Any of the above methods can be employed, but since method (1) is more advantageous from the point of raw material availability, this method will be explained in greater detail below.

Some specific examples of preparing the monomers using hydroxyethyl-methacrylate or chloroethylmethacrylate as the starting material are illustrated.

1-i. Preparation of the monomer by reaction with cinnamylideneacetic acid chloride:

The reaction proceeds in accordance with the following

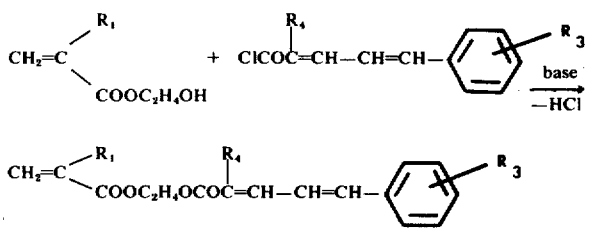

wherein $R_1$ is methyl and $R_3$ and $R_4$ are as above-defined.

This reaction is conducted using the acid chloride in an amount of 0.5 to 1.5 molar equivalent to alcohol and the use of a basic catalyst is effective. Examples of suitable basic catalysts are inorganic basic catalysts, such as sodium hydroxide, potassium hydroxide, sodium carbonate, etc., and organic basic catalysts such as pyridine, alkylpyridines, quinoline, dimethylaniline, diethylaniline, methylmorpholine, triethylamine, triethylenediamine, basic ion-exchange resins, etc., and the basic catalysts are normally used in an amount necessary for removing the hydrogen chloride formed as the reaction progresses. The amount of basic catalyst generally used ranges from about 0.05 to 200 mole percent, preferably 0.5:1 to 4:1 molar equivalents to the hydroxy group to be esterified. Of course, an excessive amount of the basic organic catalyst can be used thereby acting as additional solvent in the reaction system. Where inorganic basic catalysts are used, it is desirable to employ low reaction temperatures in order to minimize hydrolysis of the ester produced. Generally a temperature ranging from about $-15°C$ to $+25°C$ is suitable for the inorganic basic catalysts and a temperature ranging from about 10°C to 80°C, preferably 25°C to 50°C, is suitable for the organic basic catalysts.

Since the reaction generally proceeds exothermically, better results are obtained by conducting the reaction under cooling with water or ice or under vigorous stirring to prevent localized over-heating in the reaction system. In this case, it is more effective for the purpose of preventing the occurrence of localized heating to conduct the reaction in a solvent. Any solvent (other than those containing active hydrogens such as alcohols, amines, etc.) e.g. ethers, ketones, halides, amides or aromatics, for example, chlorobenzene, trichloroethylene, chloroform, diethyl ether, dimethoxyethane, anisole, methylacetate, ethylacetate, cyclohexylacetate, ethyleneglycol diacetate, acetone, methyl ethyl ketone, cyclohexanone, xylene, benzene and the like, can be used as the solvent, and examples of specific suitable solvents which can be practically used as described hereinafter as solvents for preparing the functional group-containing polymer can be used in this reaction. Furthermore, it is advantageous to use the reaction solvent together with a polar solvent such as dimethylformamide, dimethylacetamide, methyl pyrrolidone, butyrolactone, diethylformamide, diethylacetamide, formylmorpholine, hexamethylphosphoramide, tetramethylurea, etc., which tends to promote the reaction.

The amount of the solvent depends greatly upon its purposes. For example, in conducting the polymerization reaction after isolating the monomer, it is advantageous in the isolation of the monomer that the concentration of the monomer in the reaction system be higher than 10 percent by weight, preferably higher than 30 percent by weight, and generally up to about 80 percent by weight. On the other hand, in conducting the polymerization reaction after forming the reaction mixture, the concentration of the monomer is more than about 3 percent by weight, preferably more than about 5 percent by weight and generally up to about 80 percent by weight. Also, in utilizing the Schotten-Baumann reaction in which a metal hydroxide is used, the esterification reaction proceeds in a heterogeneous system, but the separation can be conducted simply or easily using a solvent which is sparingly soluble in water, such as benzene, toluene, etc., and there are no particular limitations on the amount of the solvent employed in such case.

1-ii. Preparation of the monomer by reaction with cinnamylideneacetic acid:

The reaction proceeds in accordance with the following

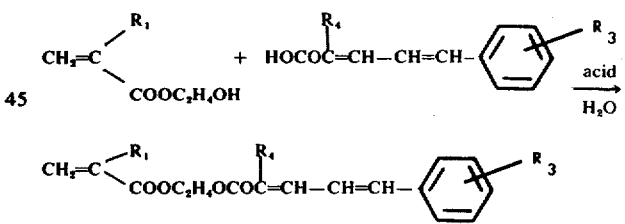

wherein $R_1$ is methyl and $R_3$ and $R_4$ are as hereinbefore defined.

This reaction is conducted by heating the reaction system above the boiling point of water in the presence of an acid catalyst. Examples of suitable acid catalysts are Lewis acids such as sulfuric acid, benzenesulfonic acid, toluenesulfonic acid, trifluoroacetic acid, etc., and the amount of the acid catalyst generally used is about 0.1 to 5 percent by weight to the amount of the hydroxy group containing compound. A suitable molar ratio of the hydroxy group containing compound to the cinnamylideneacetic acid can range from 2:1 to 1:2.

The reaction system is usually heated to temperatures above 100°C for distilling off the water formed as the reaction progresses, and it is particularly preferable in this reaction system to use a solvent capable of forming an azeotrope with water. The aforesaid solvent generally is used in an amount so that the concentration of the monomer is about 10 percent by weight, suitably 10 to 30 percent by weight. In this reaction, the occurence of side reactions by heating can be prevented by using a polymerization inhibitor such as hydroquinone, a hydroquinone monoether, a copper salt, etc., in an amount of 0.5 to 20 percent by weight to the hydroxy group containing compound.

1-iii. Preparation of the monomer by the reaction with cinnamylidene acetic acid:

The reaction proceeds in accordance with the following

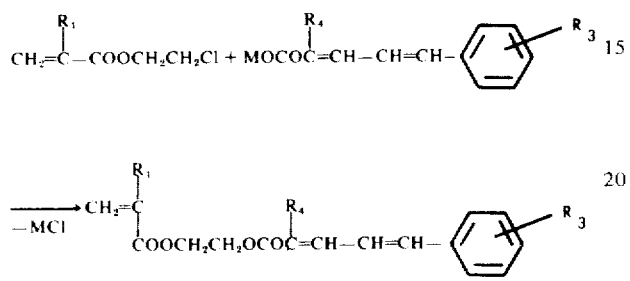

wherein $R_1$ is methyl and $R_3$ and $R_4$ are as above defined and M is sodium or potassium.

The reaction is conducted using the acid salt in an amount of 0.5 to 1.5 mole equivalent per mole of the halide (e.g., chloride, as represented above, or bromide) and a polar solvent such as dimethylformamide, dimethylacetamide, N-methylpyrrolidone, and the like, and the use of a quarternary ammonium salt such as trimethylbenzyl ammonium chloride, triethylbenzyl ammonium chloride, lauryl pyridinium bromide, and the like are generally employed. The quaternary ammonium salt is generally used in an amount of 0.1 to 10 weight percent to the weight of the halide. Where desired the halide may be used in excess amount to act as a solvent. A suitable molar ratio of the halide to the acid salt can range from about 10:1 to 1:1 with an acid salt concentration of about 10 to 30 percent by weight. Of the above-described three methods, method (1-i) is most advantageous from the standpoint of operation for the reaction since mild reaction conditions are used (e.g., the reaction proceeds smoothly at room temperature).

By homopolymerizing the monomer described above or copolymerizing the monomer with a comonomer, the functional group-containing polymer of this invention can be obtained.

The polymerization reaction or the copolymerization reaction to obtain the functional group-containing polymer is conducted in the presence of a polymerization initiator and there are no particular limitations on the type and kinds of polymerization initiators, but a radical polymerization initiator which is not influenced by moisture can be effectively used.

Examples of such polymerization initiators are peroxides, esters of peroxides, redox catalysts, persulfates, azo, e.g., α-cyano or α-carboxy azo compounds, etc. Specific examples of these initiators which are suitable include, for example, benzoyl peroxide, t-butyl peroxide, dicumyl peroxide, lauroyl peroxide, butyroyl peroxide, diisopropylpercarbonate, benzoyl glutaryl peroxide, acetyl peroxide and the like, azobisisobutyrate, azobisphenylethane, azobiscyclohexanedinitrile, azobisethylpropionate, azobisisobutyronitrile, azobisdimethylvaleronitrile, azobisamidine, potassium persulfate-sodium sulfite, azobiscyclohexanecarbonitrile, riboflavin and others such as aluminum chloride, triethylaluminum, diethylaluminum chloride, boron trifluoride, stannic chloride, boron trifluoride etherates, diethyl zinc, butyl lithium, and the like.

Of these compounds which can be effectively used as polymerization initiators at temperatures below 100°C, preferably below 80°C, are preferably used, but in particular the azo compounds which are used for conventional radical polymerization reactions are more preferred.

The amount of the polymerization initiator depends greatly upon the degree of polymerization of the polymer to be obtained and the kind of the reaction system, but will generally range from 0.01 to 10 percent by weight, preferably 0.1 to 5 percent by weight, to the weight of the monomer used. In addition, in the practice of this polymerization or copolymerization reaction, the reaction temperature and the reaction period of time can be varied, but generally a temperature of about −78°C to 80°C and a reaction time of about 5 minutes to 15 hours, respectively, is used depending on the nature of the polymerization initiator used and the polymerization conditions employed.

The polymerization or copolymerization reaction can be conducted in any desired manner such as using block polymerization, emulsion polymerization, suspension polymerization, solution polymerization, bulk polymerization, graft polymerization, dropping polymerization, etc., as desired.

Also, the polymerization reaction can be conducted under anhydrous conditions or in the presence of a gas inert to the polymerization reaction, such as a lower hydrocarbon, for example, such as methane, ethane, propane, butane, ethylene, propylene, butene, isobutylene, and the like, or mixtures of these, nitrogen, argon, etc.

The above-described conditions for the polymerization reaction can be easily determined by persons skilled in the art. Furthermore, since in the polymerization or copolymerization reaction a methacrylic acid ester or an acrylic acid ester is utilized as a polymerizable part of the monomer for preparing the functional group-containing polymer of this invention, the reaction conditions can be easily determined by one skilled in the art by reference to known reactions and conditions therefor utilized usually in the polymerization or copolymerization of acrylic acid esters or methacrylic acid esters. These conventional techniques for polymerization or copolymerization are described in many U.S. Patents, for example, as cited in Murahashi; *Synthetic Polymer;* Vol. 3, Chaper 5, (1971) published by Asakura Shoten, Tokyo or other literature sources such as T. W. Campbell *Preparative Methods of Polymer Chemistry*, John Wiley & Sons, New York (1962), and H. Mark *Encyclopedia of Polymer Science and Technology*, Interscience New York (1967).

It is assumed that in the case of conducting the radical polymerization reaction, the portion of the cinnamylideneacetic acid ester is polymerized as an internal olefin and a gelation product is obtained. In fact, it was confirmed in 1960 that a cinnamylideneacetic acid ester was polymerized as described in *Chim. e ind.*, 42, 1361, Milan.

The precise reaction mechanism for forming the soluble polymer using the radical polymerization of the monomer as in this invention has not yet been clarified.

It is, however, believed from the experimental results unexpectedly obtained in the inventors' experiments that the difference in reactivity for the radical polymerization reaction between the methacrylic acid ester portion or the acrylic acid ester portion and the cinnamylideneacetic acid ester portion is unexpectedly high and from the standpoint of reaction rate the cinnamylideneacetic acid ester portion (inner butadienyl group) does not substantially contribute to the polymerization reaction.

To obtain a homogeneous polymer or homogeneous polymer composition, it is preferable that the polymerization reaction of the monomer be conducted, where desired, in the presence of other polymers and/or materials desired to be present in the polymer composition. Suitable examples of other polymers and materials which can be present during the polymerization reaction are polymers such as ethylene-vinylacetate copolymer, polyvinylacetate, polyvinylpyrrolidone, polymethylmethacrylate or polyvinyl acetal, dyes, or pigments, such as quinacridone, phthalocyanine, phthalocyanine blue or porphyrin metal complexes, etc. If polymerization is conducted in the presence of these materials, the compatibility and uniformity are improved to a great extent in comparison with these properties when the polymer is mixed with these materials after polymerization. Additional explanation will be presented in greater detail hereinafter.

For instance, in conducting the copolymerization reaction, the monomer present in the copolymerization system can be selected from $\alpha,\beta$-unsaturated acid derivatives, olefins, halogenated olefins, vinyl esters, vinyl ethers, vinyl aromatics, vinyl heterocyclic compounds, unsaturated nitriles, etc., on considering the reacitivity of the monomer. Specific examples of such monomers are monomers such as acrylic acid esters, methacrylic acid esters, acrylic acid amides and methacrylic amides such as acrylamide, hydroxyethyl acrylate, ethyl acrylate, butyl acrylate, cellosolve acrylate ethylhexyl acrylate, methyl methacrylate, $\beta$-ethoxyethoxyethylmethacrylate, pentafluoropropylmethacrylate, pentafluoroethoxyethylacrylate, $\beta$-methacryloxyethyldimethylammonium chloride, $\beta$-acryloxyethylmonosuccinate, diacetone acrylamide, acroyl morpholine, methacrylamide, ethyl methacrylate, sulfopropyl methacrylate, cyclohexyl methacrylate, benzyl methacrylate, lauryl methacrylate, ethylene, butadiene, isoprene, chloroprene, acrylonitrile, styrene, chlorostyrene, dichlorostyrene, vinyltoluene, acetylstyrene, vinylbenzophenone, vinylpyridine, vinylimidazole, vinylmethylpyridine, vinylmethylimidazole, vinylcarbazole, vinylpyrrolidone, vinylbenzenesulfonic acid, potassium vinylbenzenesulfonate, vinyl acetate, maleic anhydride, vinyl propionate, $\beta$-cinnamoyl oxyethyl methacrylate, $\beta$-indoxylacetyloxyethyl acrylate, $\beta$-phenylacetoxy ethyl acrylate, $\beta$-phenoxyacetoxyethyl methacrylate, vinyl butyl ether, vinyl chloroethyl ether, vinylbenzene sulfonylazide, vinylisobutyl ether, monomeric silanes as described in U.S. Pat. No. 3,758,306 and the like.

Of course other functional group containing monomers such as p-vinylbenzenesulfonylazide, $\beta$-methacryloxyethylbenzenesulfonate, $\beta$-acryloxyethyltoluenesulfonate, $\beta$-cinnamoyloxyethylmethacrylate, $\beta$-acryloxyethylchloropropyl-p-chlorocinnamate, may be copolymerized in combination with the monomer described above.

The amount of the above-described monomer may be varied over a wide range depending on the properties desired in the functional group containing polymer produced.

It is known that in the case of producing a copolymer, the film forming ability, dyeability, oleophilic properties, flexibility, viscosity, glass transition point, watersolubility, solubility in organic solvents, solvent resistance, dispersibility hygroscopic properties, etc., of the copolymer produced are varied depending on the nature and the amount of comonomer or comonomers used.

For instance, the water-soluble functional group-containing polymer of this invention can be obtained by polymerizing the monomer of the formula (II), which is prepared by reaction (1-i) using a monomer selected from, e.g., acrylamide, acrylic acid, acryloylmorpholine, diacetone acrylamide, acryloxyethylmorpholine, methacryloylmorpholine, vinylmethylimidazolemethyl tosylate, sulfopropyl acrylate methacrylic acid, phosphoethyl methacrylate, vinyloxazolidone, vinylsulfonic acid, vinylpyrrolidone, vinylbenzenesulfonic acid, maleic anhydride, ethylene glycol monoacrylate, methylvinyl ketone, propylene glycol monomethacrylate, diethylene glycol monomethacrylate, p-vinylbenzyltrimethyl ammonium chloride, $\beta$-methoxyethoxyethyl methacrylate, etc. The selection of the appropriate monomer can be readily accomplished using simple routine procedures. In the case of copolymerization, however, it is necessary that the acrylate or methacrylate of this invention be included in the functional group-containing polymer in an amount effective for the cross-linking reaction. That is to say, it is necessary that the amount of the acrylate or the methacrylate be higher than 0.1 mol percent, preferably higher than 1 mol percent in the copolymerization system. Up to 100 mol percent can be suitably used.

Furthermore, in the case of conducting the polymerization or copolymerization reaction using a solvent, the solvent necessary in the reaction system can be selected from water, alcohols, halogenated hydrocarbons, aromatic compounds, ethers, esters, amides, ketones, sulfones, etc. Specific examples of such solvents are ethanol, triclene, methylene chloride, chlorobenzene, benzene, xylene, anisole, tetrahydrofuran, methyl acetate, ethyl acetate, butyl acetate, hexyl acetate, dichlorobenzene, ethylene glycol, dimethyl ether, methoxyethanol, butoxyethyl acetate, dimethylformamide, dimethylacetamide, methyl ethyl ketone, methyl isobutyl ketone, sulforane, methylpyrrolidone, hexamethylphosphoramide, ethylene carbonate, bischloroethyl ether, etc. These solvents can be suitable selected as desired.

The amount of the solvent employed in the polymerization or copolymerization reaction depends upon the purposes and properties of the desired functional group-containing polymer produced. For instance, in using the polymerization product system per se as a solution without separating the product containing the functional group-containing polymer for paints, photoresist materials, etc., the amount of the solvent is higher than about 0.1 percent by weight, preferably higher than 10 percent by weight up to about 99.5%. On the other hand, when the functional group-containing polymer produced is to be separated from the reaction product system before use, the amount of the solvent can be higher than about 5 percent by weight from the standpoint of economics and suitably up to about 99.5 percent by weight.

B. Method utilized the polymer reaction:

The functional group-containing polymer of this invention can also prepared by copolymerizing an acrylate or methacrylate each having an hydroxyl group to form a copolymer and then reacting the copolymer with a cinnamylideneacetic acid halide.

In this case, the copolymerization is conducted under conditions as described above using, as the starting material, a compound represented by the formula

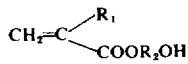

wherein $R_1$ and $R_2$ have the same significance as defined above. In the case of conducting the reaction with cinnamylideneacetic acid halide, the use of an inorganic base is not advantageous but the use of the basic catalyst as state above, preferably an organic base, is effective.

In this case, if homopolymerization of the acrylate or methacrylate, each having a hydroxyl group, is conducted, the polymer product which is soluble only in a polar solvent such as dimethylformamide, dimethylacetamide, N-methylpyrrolidone, hexamethylphosphoramide, etc., is obtained. That is to say, for such a product ordinary solvents or a mixture of ordinary solvents and polar solvents cannot be used and thus such a product is quite inconvenient, see for example, U.S. Pat. No. 3,575,946.

On the other hand, when a monomer capable of providing a polymer which is soluble in ordinary in ordinary solvents such as an acrylic acid alkyl ester, a methacrylic acid alkyl ester, styrene, etc., is used together with a hydroxyl group-containing acrylate or methacrylate in an amount of 20 to 80 mol percent, preferably 40 to 60 mol percent, to the acrylate or the methacrylate, the polymer produced is soluble in, e.g., a 1:1 volume mixture of methyl ethyl ketone and dimethylformamide, a 1:1 volume mixture of ethyl acetate and dimethylacetamide, etc., and thus the range of solvents which can be used for the reaction can be greatly increased.

In the polymer reaction, it is necessary to use the acid halide in an excessive amount to the high molecular weight alcohol, i.e., in an amount of 1.2 to 2 times the theoretical amount necessary for forming the expected ester.

Also, the amount of the solvent necessary in the reaction is about 3 to 10 times that amount used with the low-molecular esterification.

In the esterification reaction of the polymer with the acid halide, organic bases are preferably used. Inorganic bases, such as sodium hydroxide, potassium hydroxide useful in the usual Schotten-Bauman esterification reaction are not useful in this case. That is, in the reaction of poly-β-hydroxyethylacrylate and the acid chloride, gelled by-products form as described hereinbefore.

Both methods (A) and (B) described above can be used for the preparation of the functional group-containing polymers of this invention. However, method (A) is particularly useful in that it is suitable for mass-production, homogeneous products can be easily obtained, the properties of the polymers produced can be easily improved, the properties of the polymers can be varied over a wide range as desired, and ordinary solvents can be used in the method.

The functional group-containing polymer of this invention thus produced, due to the action of electromagnetic waves, particle rays, ultraviolet rays, thermal radiation, etc., undergoes changes in properties such as solubility, adhesiveness, hardness, etc., between the irradiated portions and the unirradiated portions.

Although the precise reaction mechanism for this change has not yet been completely clarified, but while not desiring to be bound, the reaction mechanism could possibly be as follows: Two kinds of reaction mechanisms are possible, that is (a) an intermolecular or interpolymer addition reaction of the internal butadienyl bond to form a cyclobutane ring compound or (b) to form a addition (ladder-type) polymer.

While the polymer compound used in the present invention is particularly useful as a light sensitive composition per se, it is possible to shorten the irradiation time and to produce the desired difference in physical properties by adding, as a sensitizing agent, an aromatic carbonyl compound, an aromatic nitro compound, an aromatic quinone, a triphenyl methane, an anthrone, a nitroaniline, an acylated nitroaniline, a thiazole, a ketone, a pyrylium dye salt, a thiapyrylium dye salt, a benzothiazoline, a naphthothiazoline, a quinolizone, an acridone, a cyanine dye, a dithiolium salt, an α-ketoaldonyl compound, a diazole, a triazole, an oxazole and various photographic sensitizing dyes.

Specific examples of such useful sensitizing compounds are nitro compounds such as p-nitrodiphenyl, 5-nitro-2-aminotoluene 4-nitro-1-aminonaphthalene, 4-nitro-1-acetylaminonaphthalene, picric acid, picramide, dichloronitroaniline, nitroacenaphthene, dinitronaphthalene, trinitrofluorenone, tetranitrocarbazole, dinitrobenzoanthrazenedione, dinitrodimethylacetyl-tert-butylbenzene, dinitrostilbene disulfonic acid, trinitronaphthalene, and dinitrochalcone; carbonyl compounds such as benzanthrone, 9-anthraldehyde, acetonaphthone, xanthone, benzophenone, phenanthrenquinone, benzanthraquinone, t-butylanthraquinone, chloroanthraquinone, anthraquinone, naphthoquinone, benzophenone, furanone, 2,6-bis-p-azidobenzal-4-methyl-cyclohexanone, benzoin, pivaloin, 2-methoxy-2-phenylacetophenone, 2-ethoxy-2-phenylacetophenone, α-methylbenzoin, α-hexylbenzoin, α-allylbenzoin, α-tolylbenzoin, benzoylmethylene-N-ethyl-β-naphthothiazoline, tetramethylaminobenzophenone, tetraethylaminobenzophenone, dimethoxybenzophenone, dimethoxythiobenzophenone, 1-cyano-2-keto-3-methyl-6-bromo-3-azabenzanthrone, 1-carboethoxy-2-keta-3,4-diazabenzanthrone, 2-keto-3-methyl-1,3-diazabenzanthrone, diphthaloylnaphthalene, 2-benzoylmethylene-1-β-naphtothiazoline, 4-H-quinolizine-4-thione, tetramethylaminothiobenzophenone, thiobenzophenone, erythrosine, 6-dimethylamino-4-methyl coumarin, 2-benzoylmethylene-1-methyl-benzothiazoline, 2-nitrophthaloylmethylene-1-ethyl-benzothiazoline, dimethylcarbamoylmethyleneethylbenzothiazoline, and diethylcarbamoylmethyleneethylbenzothiazoline, compounds such as 2-benzoylmethylene-3-ethylnaphtho [1,2-d]-thiazoline, 2,5-bis-(4-dimethylaminophenyl)oxidazole, 2-(4-dimethylaminophenyl)phenanthio-(9,10)-4,5-oxazole, 2-(p-cyanobenzoylmethylene)-3-ethylnaphtho[1,2-d]thiazoline, 3-ethyl-2-[p-(trifluoromethyl)benzoylmethylene]-naphtho[1,2-d]thiazoline, 5-chloro-2-(p-cyanobenzoylmethylene)-3-ethylbenzothiazole, methyl-3-ethyl-2-benzothiazolinylidenedithioacetate, 2,6-di(p-ethoxyphenyl)-

4-(p-n-amyloxyphenyl)-thiapyrylium perchlorate, 2,4,6-triphenylpyrylium perchlorate, 4-(4-methoxyphenyl)-2,6-diphenylpyrylium perchlorate, 4-(2,4-dichlorophenyl)-2,6-diphenylpyrylium perchlorate, 2,6-bis(4-methoxyphenyl)-4-phenylpyrylium perchlorate, 6-(4-methoxyphenyl)-2,4-diphenylpyrylium perchlorate, 2-(3,4-dichlorophenyl)-4-(4-methoxyphenyl)-6-phenylpyrylium perchlorate, 4-(4-amyloxyphenyl)-2,6-bis(4-ethyl phenyl) pyrylium perchlorate, (pyrylium salts) and dyes such as methyl violet, victoria blue, and malachite green (triphenylmethane dyes), diethyldibenzothiazyanine iodide, diethyldibenzothiacarbocyanine bromide, and dimethyldibenzothiacyanine iodide (cyanine, thiocyanine dyes).

Of these sesitizers, the carbonyl compounds and nitrocompounds show good sensitizing effects and these compounds are very convenient and commercially available.

Some of these compounds are described in U.S. Pat. Nos. 2,610,120; 2,670,285; 2,670,286; 2,670,287; 2,690,966; 2,732,301; 2,835,656; 2,956,878; 3,023,100; 3,066,117; 3,141,770; 3,173,787; 3,357,831; 3,409,593; 3,418,295; 3,453,110; 3,475,617; 3,561,959; 3,575,929; 3,582,327; 3,647,470; 3,721,566; and 3,737,319; British Pat. No. 659,197; French Pat. Nos. 1,086,257; 1,089,290; 1,238,262; and 1,359,095 and in the literature such as J. Kosar *Light Sensitive Systems* John Wiley and Sons, New York, 1965.

The sensitizer basically is used in a substantially effective amount, i.e., in that amount which provides a sensitizing function. While this can be varied, the sensitizer is generally used at a level of 0.01 to 20 weight percent, preferably 0.3 to 10 weight percent, to the weight of functional group-containing polymer. The kind and the amount of the above compound to be employed can be easily selected by one skilled in the art.

When the functional group-containing polymer of this invention is used as a photosensitive coating composition by mixing the polymer with a sensitizer, the coating compositions can also contain a variety of photographic addenda well-known in the art and utilized for their known purposes.

Such addenda can be agents to modify the flexibility of the coating, agents to modify the surface characteristics of the coating, dyes and pigments to impart color to the coating, agents to modify the adhesivity of the coating to the support, antioxidants, preservatives, surface active agents, and the like.

Examples of suitable antioxidants and preservatives are hydroquinone monoether, naphthol, polyalkyl phenol, etc., and specific examples of these classes are hydroquinone benzyl ether, trimethyl phenol, dibutyl cresol, copper phthalocyanine, propyl gallate, hydroquinone lauryl ether, phloroglucine, 5-methylresorcinol, thiourea, phenylthiourea, t-octyl-hydroquinone, copper resinate, cuprous chloride, phenyl naphthylamine, phenothiazine, p-toluquinone, dinitrobenzene, tetramethoxybenzophenone, dihydroxybenzophenone, triphenyl phosphine, triphenyl phosphite, as well as those described in U.S. Pat. Nos. 2,651,584 and 2,656,271.

It is preferable to use the thermal polymerization inhibitor in an amount of about 0.01 to 5 percent by weight to the weight of the functional group-containing polymer, which is substantially effective in the combination with the amount of the sensitizer.

Examples of pigments and dyes are materials such as titanium dioxide, zinc oxide, antimony trioxide, aluminum oxide, zirconium oxide, titanium oxide phosphate, titanium sulfate, barium sulfate, calcium oxide, magnetic compounds such as iron oxide, chromium oxide, cobalt oxide or alloys of these compounds, carbon black, vinyl monomer graft carbon black, polyacetylene, phthalocyanine, phthalocyanine blue, methylene blue, Crystal Violet, pigment yellow, quinacridone, quinacridone sulfoneamide, Rhodamine B, Fuchsine, Auramine, Anthraquinone dyes such as dimesidinoanthraquinone, photoconductive compounds fluoroescent dyes and other examples as described in U.S. Pat. Nos. 3,740,219; 3,752,668; 3,752,666; 3,753,708; and 3,754,919.

Suitable plasticizers which can be used to modify the thermo-mechanical properties of the coating composition are esters such as phthalic acid esters, e.g., dimethyl phthalate, diethyl phthalate, dibutyl phthalate, diisobutyl phthalate, dioctyl phthalate, octylcapyrl phthalate, dicyclohexyl phthalate, ditridecyl phthalate, butylbenzyl phthalate, diisodecyl phalate, diaryl phthalate, etc.; glycol esters, e.g., dimethyl glycol phthalate, ethylphthalylethyl glycol, methylphthalylethyl glycol, butylphthalylbutyl glycol, triethylene glycol dicapryl ester, etc.; phosphoric acid esters, e.g., tricresyl phosphate, triphenyl phosphate, etc.; aliphatic dibasic acid esters, e.g., diisobutyl adipate, dioctyl adipate, dimethyl sebacate, dibutyl sebacate, dioctyl sebacate, dibutyl maleate, etc.; and other materials, e.g., triethyl citrate, glycerine triacetyl ester, butyl laurate, etc., sulfonamides, e.g., N-cyclohexyltoluenesulfonamide, N-lauryltoluenesulfonamide and polyvinylmethylether etc.

The amount of the plasticizer employed in the composition well also vary depending upon factors such as the particular plasticizer employed, the presence of other components in the composition, the ultimate use to which the photosensitive layer is to be put and the like. Generally, the plasticizer is employed in amount of between about 0 to 200 weight percent, preferably 10 to 30 weight percent, based on the weight of the polymer in the coating composition.

Non-light sensitive polymers can also be added to the coating compositions to serve as diluents or extenders and solid particles, such as glass micro beads having an average diameter of about 1 to 10 $\mu$ and a variety of other addenda known to those skilled in the art can be employed in the coating composition where desired.

Examples of non-light sensitive polymers which can be incorporated in the coating compositions are phenolic resins, such as thermoplastic phenol resins or solvent soluble resole resins, hydrophilic polymers such as cellulose, hydroxyethylcellulose, hydroxypropylcellulose, ethylcellulose, cellulose hydrogenphthalate, cellulose diacetate gelatin, starch, alginic acid, carboxymethyl cellulose, polyethyleneoxide, polypropyleneoxide, polytetrahydrofuran, polyethyleneimine, polyvinylalcohol, polyvinylpyrrolidone, polyvinylmethylacetamide, ethylene-sodium, acrylate copolymers, styrene-maleic anhydride copolymers or the half ester or amide derivatives thereof, polyacrylic acid, polyacrylamide, methylmethacrylate-acrylic acid copolymers, vinylacetate-crotonic acid copolymers, methyl vinyl ether-maleic anhydride copolymers, etc.

Other thermoplaastics, such as ethylene-vinylacetate copolymers chlorinated rubber chlorinated polyethylene, polyvinylformal, polyvinylacetal, polyvinylacetate, polyvinylchloride, polytetrafluoroethylene, polyethylene beads, polydimethylsiloxane, styrene-butadiene rubbers, silicone rubbers, polyisoprene, cyclized rubber, nylon 6, nylon 10, nylon 6-6, polyvinyltoluene, polychlorostyrene, alkyd resins, epoxyresins, polyurethanes, urethane elastomers, polyethylene adipate, polymer latexes such as are described in U.S. Pat. Nos. 3,411,911, 3,488,708, 3,411,912, 3,220,844, 3,193,382 and the like. These additional polymeric materials can constitute up to 80 percent by weight of the polymeric components of the coating composition. These polymers are applied to modify the physical properties, to serve as a diluent, to adjust certain layer properties such as solubility, flexibility, anchorage, abrasion resistance, developability, and to improve the resistance of the polymer composition to etchants. Also polyfunctional unsaturated derivatives such as α,β-unsaturated acid derivatives can be used, if desired, in combination with the polymer of this invention to accelerate image formation. Suitable examples of such polyfunctional α,β-unsaturated acid derivatives are, for example, ethylene glycol dimethaacrylate, pentaerythrytol tetraacrylate, ethylenediaminediacrylate, paraphenylenediamine disorbamide, triethyleneglycoldiacrylate, glycerin trimethacrylate, ethyleneglycoldiacrylate, triethyleneglycoldimethacrylate, propanedioldiacrylate, propyleneglycoldicinnamate, neopentylglycoldimethacrylate, divinylbenzophenone, diallylbenzene, diallylphthalate, tetraallylpimelate, divinylphthalate, and the like. Particularly preferred examples are those examples which contain a number of polymerizable groups so that branching and crosslinking of the polymer formed can occur. Some of these monomers are described in U.S. Pat. Nos. 3,448,089; 3,389,831; 3,733,200; 3,753,720; and the like.

Active methylene compounds, couplers or leuco dyes can be used to obtain a mono- or multi-colored image. Couplers are well-known in the field of color photography. Some of these are described in U.S. Pat. Nos. 3,227,554; 3,419,391; 3,694,214; 3,703,375; 3,704,125 and the like.

N-halocyclicimides such as N-bromosuccinimide, N-chlorophthalimide can also be used. Organic azides such as arylazides, arylsulfonyl azides and preferably polyazides such as diazidostilbene, phenylenebisazide, terephthaloylazide, benzenedisulfonylazide, naphthalenedisulfonylazide, diazidochalcone, ethyl-p-azidocinnamylideneacetate, diazido-benzophenone, o-quinoneazide, may be used. Some of these are described U.S. Pat. Nos. 3,752,671; 3,758,303; and 3,711,285, etc.

The optimum amounts of these components described above and others can be readily determined by those skilled in the art taking the preceeding techniques and description into consideration.

These additives can generally be used in an amount of about 0 to 90 percent, preferably 0.5 to 40 percent by weight, depending on the purposes of use of the resin composition and within the range that the additive or additives can be uniformly dispersed.

As described above, the functional group-containing polymers of this invention can be used as materials for paints, photographic duplications, printing plates, resists, relief images, etc. The forming of images using the function group-containing polymer of this invention, which is one of the uses thereof, will then be explained in detail hereinafter.

The functional group-containing polymer of this invention is dissolved or dispersed in a ketone solvent, an amide solvent, a cellosolve solvent, or a halide solvent. Suitable examples include ketones such as acetone, methyl ethyl ketone, methyl isobutyl ketone, cyclohexanone, diisobutyl ketone, acetylacetone, hexanedione, 4-butyrolactone, acetophenone, etc. esters such as 2-ethoxyethylacetate, 2-methoxyethylacetate, ethoxypropylacetate, butoxypropylpropionate, phenoxypropylacetate, furfurylacetate, cyclohexylacetate, benzylacetate, ethyl acetate, butyl acetate, n-amyl acetate, methyl formate, ethyl propionate, dimethyl phthalate, ethyl benzoate, etc.; aromatic hydrocarbons such as toluene, xylene, benzene, ethylbenzene, etc.; fluorinated alcohols such as trifluoroethanol, tetrafluoropropanol, etc.; halogenated hydrocarbons such as carbon tetrachloride, trichloroethylene, chloroform, 1,1,1-trichloroethane, chlorobenzene, dichlorobenzene, etc.; ethers such as dimethoxyethane, dimethoxypropane, diethyleneglycoldimethyl ether, tetrahydrofuran, anisole, diethyl ether, ethylene glycol monomethyl ether, ethylene glycol monoethyl ether, acetate, sulfur containing solvents such as formylmorpholine, dimethylformamide, dimethylacetamide, pyrrolidone, butyrolactone, hexamethylphosphoramide, methylphenylsulfone, sulforane, dimethyl sulfoxide, methylpyrrolidone, hexaethylphosphoramide, etc., or in a mixture of such solvents. The solvent solution, in an amount of 0.1 to 95%, preferably 1 to 45%, by weight of solvent, can be used, together, if desired, with additives such as a stabilizer, a plasticizer, a dye, a pigment, a sensitizer, a wetting agent such as is described in U.S. Pat. No. 3,753,715, and other polymers as described above.

The solution thus prepared is coated on a support such as a plastic film, e.g., a film of polyvinyl acetal, nylon-6, nylon-6,6, nylon-10, polyethylene, polypropylene, polyalkylmethacrylate, polycarbonate, polytetrafluoroethylene, polybutyleneterephthalate, polyethylene naphthalate, polyethylene terephthalate, cellulose acetate, cellulose acetate butyrate, cellulose propionate, etc., a polymer coated paper; a metal sheet, e.g., a zinc sheet, a copper plate, etc., a magnesium foil, a silver foil, an aluminum sheet, silicon wafer, etc. or a glass plate a photoconductive wafer or ceramics in a thickness of 0.2 to 300 microns, preferably 0.2 to 8 microns, using conventional coating techniques such as dip coating, coating rod, spinner coating, spray coating, extrusion coating, laminating, vacuum evaporation, etc., to form a photosensitive layer. The optimum coating thickness for a particular purpose will depend on such factors as the use to which the coating will be put, the particular light-sensitive composition employed, and the nature of other components which may be present in the coating solution. If desired, a protective layer (such as a cellophane layer, a polyethylene terephthalate layer) can be formed on the photosensitive layer. If desired, the coating composition can be first coated on a temporary support and then transferred, e.g., by thermal lamination to the support where it is to be used, either uniformly or in an imagewise fashion. Such transfer techniques are described, for example, in U.S. Pat. Nos. 3,060,023; 3,346,383; and 3,469,982, etc.

Photomechanical images can be prepared with the coated layer on a support by imagewise exposing the layer to a light source to harden or insolubilize the functional group-containing polymer in the exposed areas while superposing thereon an original to be duplicated.

The exposure can be carried out using the irradiation of a mercury lamp, a high pressure mercury lamp, a carbon arc lamp, fluorescent lamp with ultraviolet light emitting phosphors, a cathode ray tube, a laser beam, an argon glow lamp, a tungsten lamp, a photoflood lamp, an electron beam, ultraviolet rays, a xenon lamp, etc. as the energy source.

The irradiation time can be easily varied depending upon the energy source, the distance of the light source from the photosensitive material, the sensitizer employed, the thickness of the layer, the content of the sensitizer, the pigment content, the character of image being reproduced and the like. Exposures of from 0.01 second to several minutes, e.g., about 6, are generally adequate.

The exposed plate, if desired, is then processed with a solvent to selectively remove portions, and if desired, the developing solution can contain a dye or a pigment to obtain more distinct image formation. Conventional processing procedures used, in general, for light-sensitive systems (as disclosed, for example, in Kosar *Light Sensitive Systems*, John Wiley & Sons (1965)) can be employed with only minor modification. The polymer compound at the non-irradiated areas does not undergo a photo hardening reaction and is dissolved in the solvent, to which areas the dye or pigment adheres to form images. Such solvents can be selected from those solvents set forth above in detail as suitable coating solvents as well as other solvents or solutions such as alkaline aqueous solutions, acidic aqueous solutions and the like.

In an alternate embodiment using the light-sensitive material of this invention, an image can be formed by exposure as described above and then the exposed element developed by heating to a temperature in the range of about 50° to 200°C, which is intermediate between the point at which the polymer becomes tacky in the unexposed areas and the exposed areas to soften or render the polymer tacky in the exposed areas. The softened polymer can then be toned or transferred to a receiving sheet under pressure and toned or transferred without toning if a pigment, dye or color forming compound is incorporated in the original layer.

to further facilitate an understanding of this invention, the invention will additionally be explained more specifically and in greater detail by reference to the following examples of image formation as an embodiment of the application of the functional group-containing polymer or the functional group-containing polymer composition of this invention.

In addition, it will be easily understood that the use of the functional group-containing polymer or functional group-containing polymer composition of this invention is not limited to the embodiments shown in the examples.

Examples of the preparation of the monomers for preparing the functional group-containing polymers of this invention and the preparation of the functional group-containing polymers of this invention are illustrated below.

MONOMER PREPARATION EXAMPLE 1

8.7 g of cinnamylideneacetic acid was added to 100 ml of benzene and then an excessive amount of thionyl chloride (1.2 molar equivalent to cinnamylideneacetic acid) was added dropwise to the mixture while heating to 70°–90°C and stirring the mixture to form a cinnamylideneacetic acid chloride. By distilling off the solvent from the reaction product, yellow crystals having a melting point of about 60°C were obtained. The crystals were dissolved in 20 ml of methyl ethyl ketone and then 8 g of hydroxyethyl methacrylate was added slowly to the solution with stirring under ice-cooling. After further stirring under ice-cooling for about 20 minutes, 50 ml of pyridine was added slowly to the mixture as a hydrogen chloride accepting agent to conduct esterification. When the reaction product was treated with diluted (5%) hydrochloric acid, crystals were formed, which were recovered and recrystallized from hexane to provide crystals of a monomer having a melting point of 51° – 52.5°C with a yield of 94%.

Elementary analysis for C and H: Calculated: C 71.30%; H 6.33%. Found: C 71.32%; H 6.28%.

MONOMER PREPARATION EXAMPLE 2

By repeating the same procedure as described above using 2-hydroxy-3-chloropropyl methacrylate in place of the hydroxyethyl methacrylate, a light-yellowish product was obtained.

POLYMER PREPARATION EXAMPLE 1

2 g of the compound prepared in Monomer Preparation Example 1 as described above, 2.0 g of lauryl methacrylate, and 0.6 g of methyl methacrylate wee dissolved in 10 ml of methyl ethyl ketone and after adding to the solution 30 mg of azobisdimethylvaleronitrile as a polymerization initiator, the polymerization reaction was conventionally conducted. More specifically, the reaction system was maintained at 60° – 75°C for 25 hours and then the reaction product was poured slowly into an excessive amount of methanol, whereby a polymer was isolated as a white powder. The product thus prepared had an intrinsic viscosity of 0.12 (measured in methyl ethyl ketone at 30°C).

The product was soluble in methyl ethyl ketone and no formation of insoluble matter due gelation was observed at all.

POLYMER PREPARATION EXAMPLE 2

73 g of methyl methacrylate and 76 g of hydroxyethyl methacrylate were dissolvled in 200 ml of dimethylformamide and after adding to the solution a small amount (1.2 g) of an azo compound as a polymerization initiator, the polymerization was conducted at 60°C for 3 hours. Thus, a polymer was obtained with a yield of 92% and the intrinsic viscosity of the product in dimethylformamide at 30°C was 0.28.

Then, 5 g of the thus obtained polymer containing hydroxyl groups was dissolved in a mixture of 16 ml of methyl ethyl ketone and 9 ml of dimethylformamide and the solution prepared was mixed with 10 ml of a methyl ethyl ketone solutions containing 0.02 mol of cinnamylideneacetic acid chloride under ice-cooling. Then, after stirring the mixture for about 20 minutes, 20 ml of pyridine was added dropwise to the mixture to remove the hydrogen chloride formed. The reaction product was treated with an ice-cooled diluted (5%) hydrochloric acid solution to remove the soluble matter and then the polymer product thus precipitated was recovered and re-precipitated from a mixture of methyl ethyl ketone and methanol (8:50 by volume). By vacuum drying the product, 7.5 g of the desired functional group-containing polymer was obtained.

The polymer thus obtained exhibited almost no absorption due to the presence of a hydroxyl group in the infrared absorption spectra thereof, which indicated the reaction having proceeded quantitatively.

EXAMPLE 1

100 mg of the product obtained in Polymer Preparation Example 1 as described above was dissolved and then 8 mg of 5-nitroacenaphthene, as a sensitizer, was added to the solution to provide a photosensitive composition. The photosensitive composition was coated on a surface-treated aluminum sheet in a dry thickness of about 3 microns using dip coating and after air drying, the photosensitive layer was dried under heating, e.g., at 50° to 90°C.

A line image original was placed on the photosensitive layer and the assembly was exposed for 1 minute to radiation from a high prepssure mercury lamp of 450 watt at a distance of 30 cm from the assembly. Then, the photosensitive layer thus exposed was treated with a solvent using dimethylformamide to remove the uncured or unexposed portions. Then the remaining layer was dyed with a oily dye (Oil Blue G Extra (CI-61525)), whereby the exposed portions could be observed as a clear blue image.

When Michler's ketone was used in place of the nitroacenaphthene, a similar image was formed with a similar image exposure of 1 minute.

Furthermore, when another oily dye was used in the above procedure, a clear image was also obtained.

When the above procedures were repeated without using 5-nitroacemaphthene, a similar image was obtained by exposing the photosensitive layer for about 30 minutes.

EXAMPLE 2

25 mg of the product obtained in Polymer Preparation Example 2 as described above was dissolved in 0.5 ml of dimethylformamide, and after adding each of the following sensitizers to the polymer containing solution, the same procedure as described in Example 1 was conducted. The sensitizers and the amounts thereof were as follows: 2 mg of 5-nitroacenaphthene, 5 mg of tetranitrofluorenone, 3 mg of N-methyl-2-benzoylmethylene-β-naphthothiazoline, 2 mg of phenanthrene quinone, and 1.5 mg of diethylaminobenzophenone.

On using all of the above-described sensitizers, the photosensitive layer was insolubilized at the exposed portions with a similar exposure as in Example 1 of about 30 seconds and the exposed portions retained their olephilic property.

While the invention has been described in detail and with reference to specific embodiments thereof, it will be apparent to one skilled in the art that various changes and modifications can be made therein without departing from the spirit and scope thereof.

What is claimed is:

1. A monomer represented by the following formula

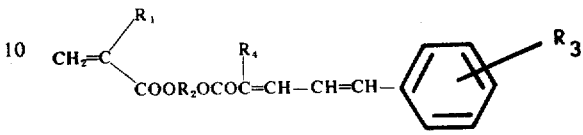

wherein $R_1$ represents a hydrogen atom or a methyl group; $R_2$ represents $-CH_2CH_2-$, $-CH_2CH_2CH_2-$, $-CH_2CH_2CH_2CH_2-$,

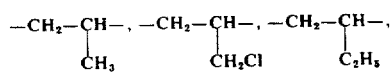

$-CH_2CH_2OCH_2CH_2-$,

$-CH_2CH_2OCH_2CH_2OCH_2CH-$,
$-CH_2CH_2CH_2CH_2CH_2CH_2-$,

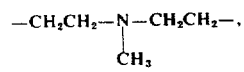

$-CH_2CH_2SCH_2CH_2-$, $-C_6H_{10}-$, $-C_6H_4-$, $-CH_2C_6H_4CH_2-$, or $-CH_2C_6H_{10}CH_2-$; $R_3$ is a hydrogen atom, a halogen atom, a methoxy group, a nitro group or a methyl group; $R_4$ is a hydrogen atom, a cyano group or a carbamoyl group.

2. The monomer of claim 1, wherein $R_2$ is $-CH_2CH_2-$, $-CH_2CH_2CH_2-$, $-CH_2CH_2CH_2CH_2-$,

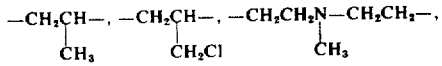

$-CH_2CH_2OCH_2CH_2OCH_2CH_2-$,

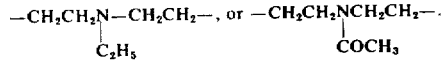

* * * * *